US00PP22974P3

(12) United States Plant Patent
Grard et al.

(10) Patent No.: US PP22,974 P3
(45) Date of Patent: Aug. 21, 2012

(54) APPLE TREE NAMED 'GRADIYEL'

(50) Latin Name: ***Malus domestica* (Borkh.)**
Varietal Denomination: Gradiyel

(76) Inventors: Alexandre Grard, Mudaison (FR); Olivier Grard, Mudaison (FR)

( * ) Notice: Subject to any disclaimer, the term of this patent is extended or adjusted under 35 U.S.C. 154(b) by 0 days.

(21) Appl. No.: 12/807,457

(22) Filed: Sep. 3, 2010

(65) Prior Publication Data

US 2011/0126330 P1 May 26, 2011

Related U.S. Application Data

(60) Provisional application No. 61/276,488, filed on Sep. 11, 2009.

(51) Int. Cl.
*A01H 5/00* (2006.01)

(52) U.S. Cl. ..... Plt./161

(58) Field of Classification Search ..... Plt./161
See application file for complete search history.

(56) References Cited

OTHER PUBLICATIONS

GTITM UPOVROM Citation for 'Gradiyel' as per QZ PBR20042211; Nov. 15, 2004.*
GTITM UPOVROM Citation for 'Gradiyel' as per CH PBR08-2491; May 9, 2008.*
GTITM UPOVROM Citation for 'Gradiyel' as per FR NLI1016475; Feb. 20, 2006.*

* cited by examiner

*Primary Examiner* — Kent L Bell
(74) *Attorney, Agent, or Firm* — Ballew Law

(57) ABSTRACT

'Gradiyel' is a new and distinct apple tree notable for its semi-upright plant habit, freely flowering and fruiting habit, mid-season flowering time, and high storage capacity.

3 Drawing Sheets

Latin name of the genus and species of the plant claimed: *Malus domestica* (Borkh.).

Variety denomination: 'Gradiyel'.

CROSS REFERENCE TO RELATED APPLICATIONS

This application claims priority of co-pending U.S. Provisional Application Ser. No. 61/276,488 filed Sep. 11, 2009.

STATEMENT REGARDING FEDERALLY SPONSORED RESEARCH OR DEVELOPMENT

None

BACKGROUND OF THE INVENTION

The present invention relates to a new and distinct cultivar of apple tree, botanically known as *Malus domestica*, and hereinafter referred to by the name 'Gradiyel'.

The new apple variety 'Gradiyel' originated from a controlled cross in Hérault, France of *Malus domestica* 'Christmas Rose', (not patented), as the female, or seed parent, with *Malus domestica*, 'Gradigold', (not patented) as the male or pollen, parent. The new Apple tree was discovered and selected by the inventors as a single plant from within the progeny of the stated cross-pollination in a controlled environment in Hérault, France in 1991.

Asexual propagation by grafting was first carried out in Maguio, France. Gradirose has been asexually reproduced by budding and grafting, since 1994 in Hérault, France, and has demonstrated that the new variety reproduces true to type with all of the characteristics, as herein described, firmly fixed and retained through successive generations.

SUMMARY OF THE INVENTION

The following characteristics of the new variety have been repeatedly observed and can be used to distinguish 'Gradiyel' as a new and distinct cultivar of apple:

1. Semi-upright plant habit.
2. Freely flowering and fruiting habit.
3. Mid-season flowering time.
4. High storage capacity.

'Gradiyel' can be compared to Golden Delicious (not patented). Fruit of the new variety is mature and ready for harvest about 20 days after the fruit of Golden Delicious. The fruit skin of 'Gradiyel' has more than 50% pink blush whereas the fruit skin of Golden Delicious has less than 10% pink blush. The fruit of 'Gradiyel' has a longer shelf life than Golden Delicious, and a sweeter flavor.

BRIEF DESCRIPTION OF THE PHOTOGRAPHS

Figure 1:
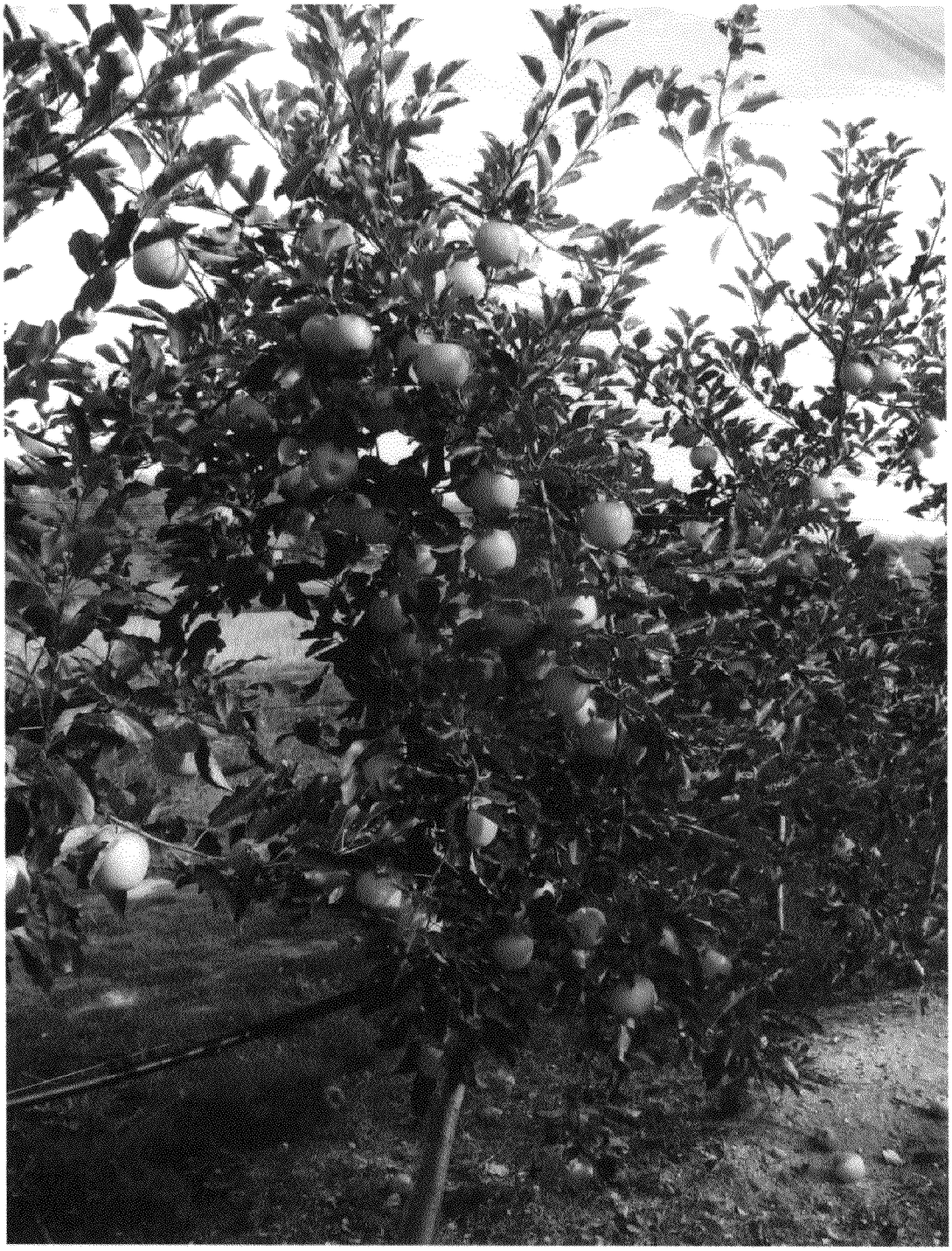
Figure 2:
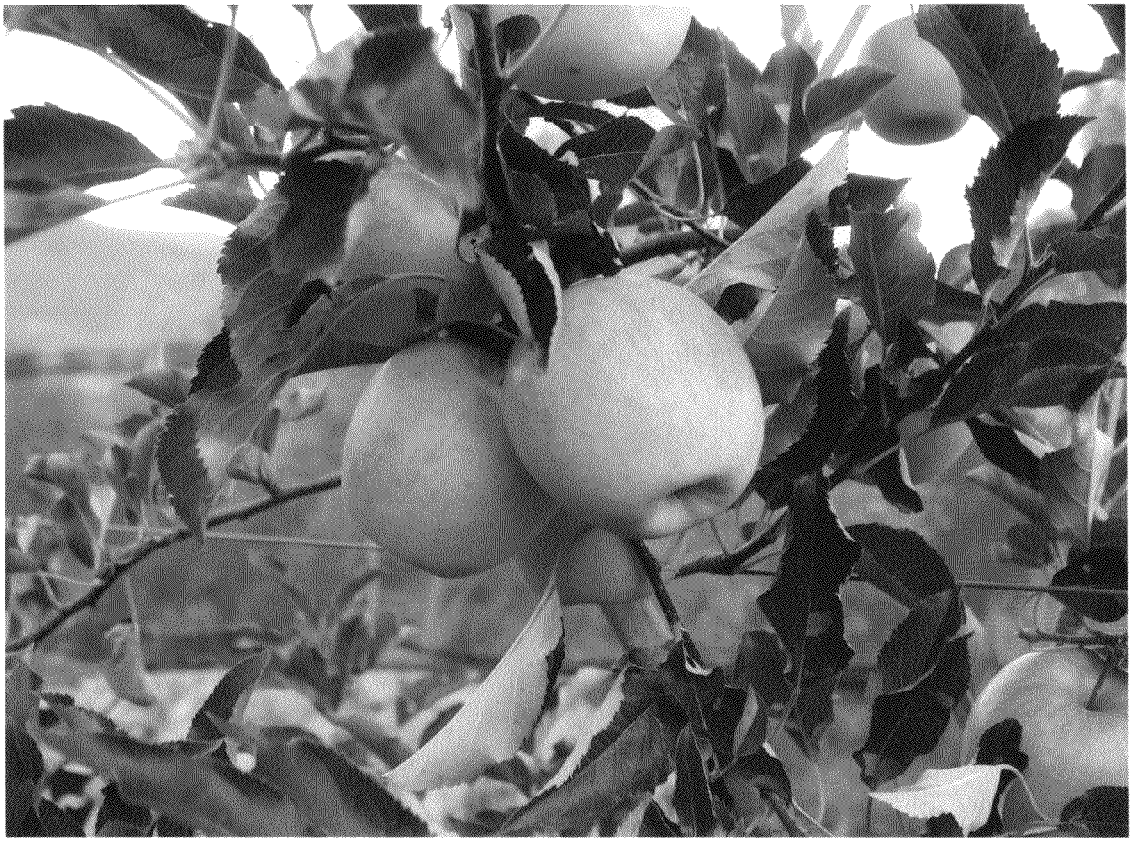
Figure 3:
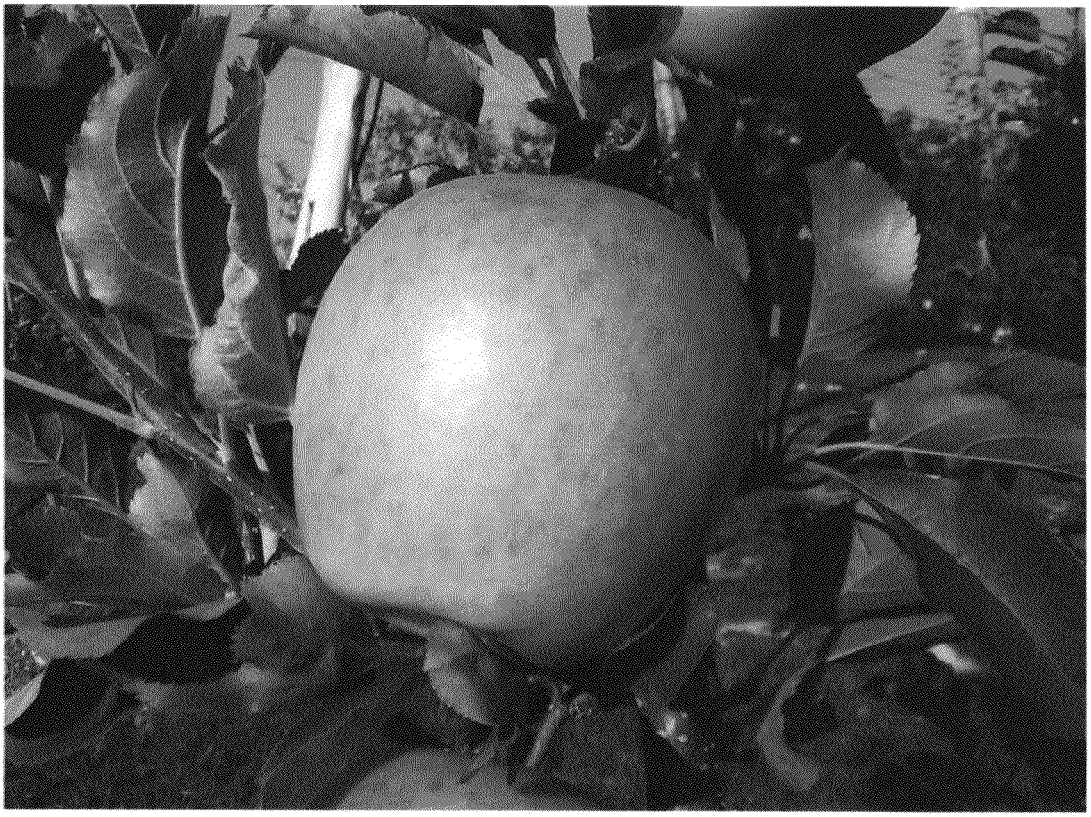

FIG. 1 shows the tree of the new variety with fruit;
FIG. 2 shows the branch and fruit of the new variety; and
FIG. 3 shows the fruit of the new variety.

DETAILED BOTANICAL DESCRIPTION

The following detailed botanical description is based on observations of trees planted in 1995, and described during the 2003 and 2004 growing seasons at Hérault, France. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Botanical classification: *Malus domestica* Borkh cultivar Gradiyel.

Parentage:

*Female, or seed parent.*—*Malus domestica* 'Christmas Rose', not patented.

*Male, or pollen, parent.*—*Malus domestica* 'Gradigold' not patented.

Tree:

*Vigor.*—Vigorous.

*Habit.*—Semi-Upright.

*Size.*—Height: 3.0 m.

*Bearing.*—Annual bearing habit on spurs and long shoots.

*Trunk.*—Diameter: 12-18 cm at 30 cm above graft union; bark texture smooth; color brown RHS 200C; Lenticels absent.

*Winter hardiness.*—Hardy in area tested.

*Branches.*—1 m above graft union; length 180 cm; diameter 5-7 cm; crotch angle 70°; color light brown RHS 200D; Approximately 12 branches per tree; Texture smooth, very hard; Internode length medium long; Lenticels medium to high density 8- 10 per $cm^2$; Color white RHS 155D; Diameter 8-10 mm.

Dormant one year old shoot:

*Size.*—Diameter 5-6 mm; Length 30-40 cm.

*Color.*—Brown RHS 200C.

*Internode length.*—About 3 cm.

*Pubescence.*—Weak.

*Lenticels.*—Length 0.9-1.2 mm, width 0.9-1.1 mm; Density 2-4/$cm^2$; Color yellow white RHS 158C.

Flowers:

*Bud.*—Quantity per spur 3-4; length 9-11 mm; Diameter 9-11 mm shape slightly pointed; color red-purple RHS 63A.

*Petals.*—Shape round; Quantity per flower 5; Margins free to touching, entire; Texture smooth; Length 19-20 mm; Width 13-14 mm Apex shape slightly pointed; Base shape round; upper surface color white RHS N155C; Lower surface color red RHS 56D when fully open.

*Flower.*—Diameter of fully open flower 2-2.5 cm; Quantity per cluster 4; Fragrance faint; Height 0.6-0.9 cm.

*Sepals.*—Quantity per flower 5; Shape triangular; Upper surface color green RHS 135B.

*Pedicel.*—Length 18-20 mm; Diameter 1-2 mm; Color greyed-purple RHS 187A.

*Pistil.*—Length 12-13 mm; Color yellow-green RHS 145D.

*Anthers.*—Quantity per flower 15-16; length 2 mm; pollen color yellow RHS 12C.

*Stigma.*—Width 1 mm; Color RHS 11D.

*Style.*—Length 5-6 mm; color yellow-Green RHS 145D.

*Bloom period.*—Early to Mid Season; first bloom April 10, full bloom April 15 at Hérault, France.

Leaf:

*Attitude in relation to shoot.*—Upwards.

*Size.*—Length 10-11 cm; Width 2-3 cm; Length to Width Ratio 5-3.7.

*Margin.*—Serrate.

*Texture.*—Smooth.

*Pubescence.*—Upper surface weak to absent; Lower surface weak.

*Color.*—Upper surface yellow-green RHS 147B; lower surface yellow-green RHS 147C.

*Shape.*—Ovate; apex acuminate; base aequilateral.

*Veins.*—Venation Type: Net-like; Medium dense to dense; Upper surface yellow-green RHS 145A; Lower surface yellow-green RHS 145D.

*Petiole.*—Length 3-4 cm; width 0.5-1 mm; color yellow-green RHS 147D.

Fruit:

*Size.*—Weight 150 g; diameter 75-80 mm; Height 9-10 cm.

*Fruit shape.*—Globose.

*Position of maximum diameter.*—Top.

*Ribbing.*—Absent.

*Aperture of eye.*—Closed.

*Depth of eye basin.*—8-10 mm.

*Width of eye basin.*—35-40 mm.

*Stalk.*—Diameter 0.5-1 mm; length 25-28 mm; Color brown RHS 199C; Lenticels few, size 0.1 cm, color greyed-orange RHS 175C.

*Depth of stalk cavity.*—13-15 mm.

*Width of stalk cavity.*—35 mm.

*Lenticels.*—Size 0.6-0.8 mm; density 7-9/$cm^2$.

*Bloom of skin.*—Absent.

*Greasiness of skin.*—Absent.

*Ground color of skin.*—Yellow-green RHS 150C.

*Over color of skin.*—Red-purple RHS 58B.

*Skin thickness.*—Medium thick.

*Skin texture.*—Smooth.

*Skin firmness.*—Hard, crisp.

*Amount of over color.*—40-70 percent.

*Pattern of over color.*—Solid flush with weakly defined stripes.

*Flesh.*—Texture juicy, firm 7.5 kgs/$cm^2$; Aroma strong; high eating quality; rich flavor; yellow-white RHS 158D.

*Brix.*—14-16°.

*Seeds.*—Quantity per fruit 6-8; teardrop shape; seeds per locule 2; color brown RHS 200B.

*Core.*—Few bundles, Symmetrical, Length 31 mm-33 mm, Width 28 mm-30 mm.

*Locules.*—Quantity per fruit 5; length 1 cm; width 0.3-0.5 cm.

*Harvest Date.*—First Harvest Date — October 5, 2010 and last Harvest Date — October 15, 2010 in southern France.

*Production.*—40 to 60 tons of fruit produced per hectare; 80% of fruit with size 70-80 mm.

*Keeping quality.*—Good to very good, 6-8 months.

*Use.*—Fresh market.

*Resistance/susceptibility to known diseases/pests.*—Susceptible to grey aphids.

We claim:

1. A new and distinct apple tree substantially as shown and described herein.

* * * * *